(12) United States Patent
Foo et al.

(10) Patent No.: US 7,546,155 B2
(45) Date of Patent: Jun. 9, 2009

(54) EFFICIENT MULTI-SLICE ACQUISITION WITH BLACK BLOOD CONTRAST IN FAST SPIN ECHO IMAGING

(75) Inventors: Thomas K. F. Foo, Rockville, MD (US); Zahi A. Fayad, New York, NY (US)

(73) Assignees: General Electric Company, Schenectady, NY (US); Mount Sinai Medical Center, New York, NY (US)

( * ) Notice: Subject to any disclaimer, the term of this patent is extended or adjusted under 35 U.S.C. 154(b) by 1587 days.

(21) Appl. No.: 09/682,685

(22) Filed: Oct. 5, 2001

(65) Prior Publication Data

US 2003/0069493 A1 Apr. 10, 2003

(51) Int. Cl.
*A61B 5/055* (2006.01)

(52) U.S. Cl. .................... 600/410; 324/309

(58) Field of Classification Search ........... 600/410, 600/407, 419, 413; 324/300, 309, 307
See application file for complete search history.

(56) References Cited

U.S. PATENT DOCUMENTS

| 5,201,311 | A | * | 4/1993 | Bottomley et al. ......... 600/422 |
| 5,271,399 | A | | 12/1993 | Listerud et al. |
| 6,271,665 | B1 | | 8/2001 | Berr et al. |
| 6,340,887 | B1 | | 1/2002 | Liu et al. |
| 6,380,736 | B1 | | 4/2002 | Hajnal |
| 6,380,739 | B1 | | 4/2002 | Machida |
| 6,498,946 | B1 | * | 12/2002 | Foo et al. .................... 600/410 |

OTHER PUBLICATIONS

Hui hu: "Multi-slice helical CT: Scan and reconstruction", Milwaukee WI; Med.Phys. 26 (1) Jan. 1999.
Parker, dennis I: Optimization of short scan convolution reconstruction in fan beam CT; CH1751-7/82/0000/0199$00.75 © 1982 IEEE.
Simonetti OP, Finn JP, White RD, Laub G, Henry DA. "Black blood" T2-weighted inversion-recovery MR Imaging of the heart. *Radiology* 1996; 199; 49-57.

* cited by examiner

*Primary Examiner*—Ruth S Smith
(74) *Attorney, Agent, or Firm*—Ziolkowski Patent Solutions Group, SC

(57) ABSTRACT

The invention includes a technique for efficient multi-slice fast spin echo image acquisition with black blood contrast in cardiac imaging. The technique includes applying a non-selective inversion pulse, followed by a re-inversion pulse that is slice-selective over a region encompassing a plurality of slice selections. Execution of a series of RF excitation pulses with fast spin echo readout is timed such that signal from blood is near a null point before acquiring data for each spatial slice. For greater contrast consistency, the flip angles for the excitation pulses occurring before the null point can be reduced, and those occurring after the null point can be increased.

20 Claims, 3 Drawing Sheets

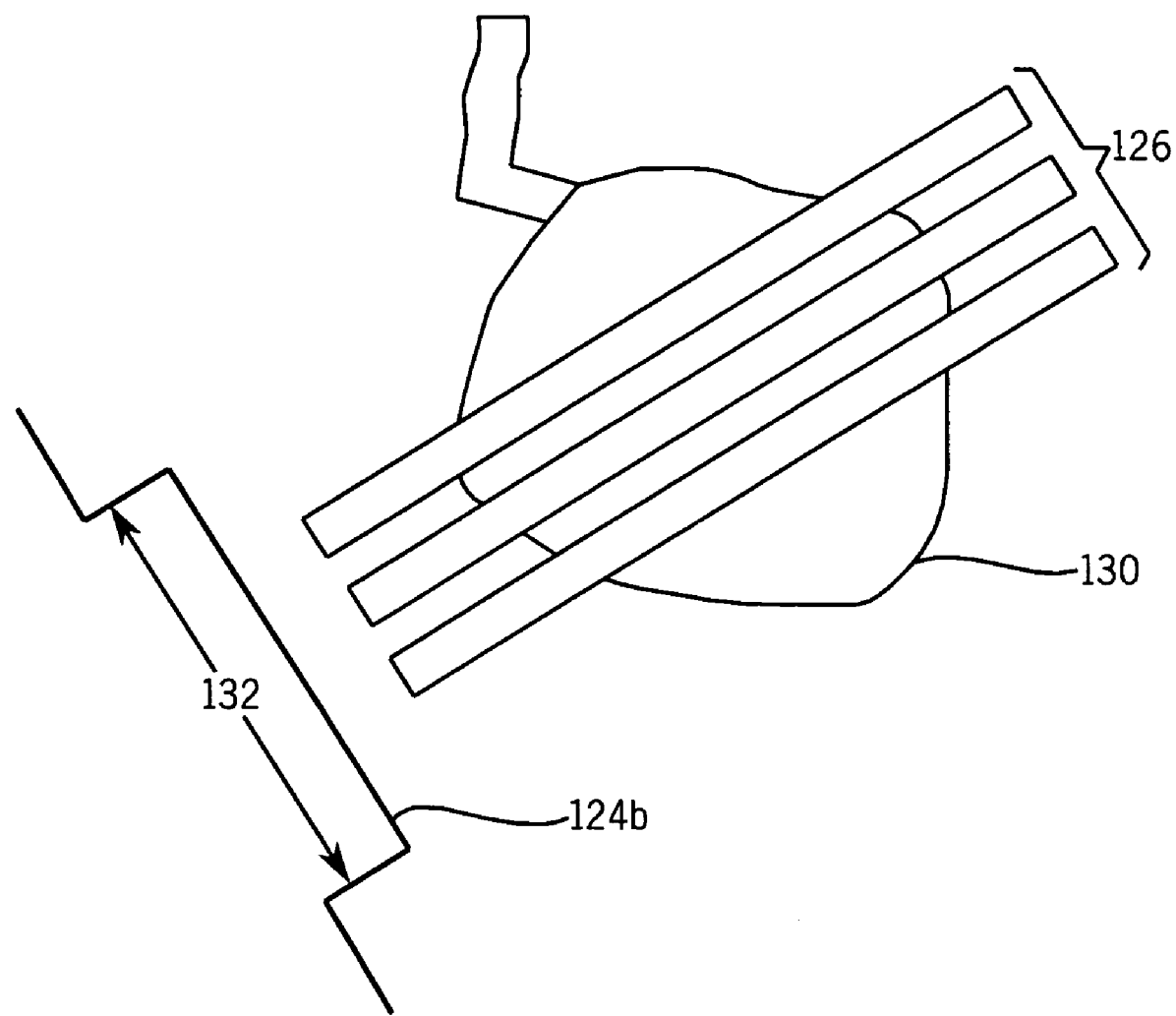

EFFICIENT MULTI-SLICE ACQUISITION WITH BLACK BLOOD CONTRAST IN FAST SPIN ECHO IMAGING

BACKGROUND OF INVENTION

The present invention relates generally to magnetic resonance imaging (MRI), and more particularly to, a pulse sequence, method, and apparatus for multi-slice acquisition using fast spin echo imaging to acquire black blood contrast images.

MRI uses radio frequency pulses and magnetic field gradients applied to a subject in a strong homogenous magnetic field to produce viewable images. When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$ may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

Current techniques for the acquisition of multi-slice fast spin echo (FSE) images require that each slice be imaged in separate breath-holds in order to attain black blood contrast in a gated sequence. Such conventional gated-FSE acquisitions are able to acquire images from only one spatial location per breath-held acquisition because the second inversion recovery RF pulse is slice selective only over the imaged slice.

It would therefore be desirable to have a technique to acquire black blood contrast images using fast spin echo acquisitions with improved multi-slice acquisition for efficient imaging that is capable of imaging across one or more R-R intervals.

BRIEF DESCRIPTION OF THE INVENTION

The present invention relates to an MR pulse sequence, apparatus, and a technique for efficient multi-slice acquisition with black blood contrast in fast spin echo imaging that solves the aforementioned problems.

The proposed technique includes a non-selective inversion RF pulse, followed by a broad-band slice selective pulse that re-inverts the spins in the slab encompassing the slices to be imaged. After an inversion time, RF excitation pulses with a fast spin echo readout are executed acquiring data for each spatial slice in an order that provides optimal blood suppression. The inversion time is preferably selected such that the blood signal is close to the null point. This technique differs from conventional gated fast spin echo imaging with black blood image contrast in that the re-inversion or tip-up pulse in the conventional technique is effective only in a single slice of interest which results in only one slice or spatial section acquired per breath-hold or acquisition. The present invention allows for multi-slice acquisition.

In accordance with one aspect of the invention, a method of multi-slice fast spin echo image acquisition with black blood contrast is disclosed that includes a non-selective inversion pulse and applying a re-inversion pulse that is slice selective over a region encompassing a plurality of slice selections. The method includes timing execution of the series of RF excitation pulses with fast spin echo readout such that signal from black blood is near a null point. Data is then acquired for each spatial slice.

In accordance with another aspect of the invention, a computer program is disclosed for multi-slice coverage in a single acquisition with black blood $T_2$- weighted image contrast. The computer program has a set of instructions that when executed by a computer cause a computer to generate and cause application of a non-selective inversion RF pulse to a slab of slices, each having a predefined thickness. The computer program also causes the computer to generate and cause application of a slice selective re-inversion RF pulse having a slice thickness greater than the predefined thickness of a single slice and apply an inversion time so that a null point of blood within the slab occurs in a middle of an acquisition. A series of RF excitation pulses is applied and MR data is acquired for each slice in the slab.

In accordance with another aspect of the invention, an MR apparatus to produce consistent contrast in FSE image acquisition is disclosed. The apparatus includes an MRI system having a number of gradient coils positioned about a bore of a magnet to impress a polarizing magnetic field and an RF transceiver system and an RF modulator controlled by a pulse control module to transmit RF signals to an RF coil assembly to acquire MR images. The MRI apparatus also includes a computer programmed to apply a pulse sequence having a non-selective inversion pulse to invert spins in a longitudinal direction across an entire slab of slices and a slice selective re-inversion pulse having an implied width at least as large as that of the non-selective inversion pulse. The pulse sequence applied by the computer also has a series of excitation pulses having fast spin echo readout spaced apart from the slice selective re-inversion pulse by an inversion time to acquire data for each slice in the slab.

In accordance with yet another aspect of the invention, a pulse sequence for use in multi-slice MR data acquisition is disclosed. The pulse sequence includes a non-selective inversion pulse applicable to a slab of slices and a slice selective re-inversion pulse applicable to at least a number of the slices in the slab of slices. The pulse sequence also includes a series of fast spin echo readout excitation pulses applicable to the at least a number of slices in the slab of slices after an inversion time. Preferably, the aforementioned inversion time is selected so that blood in the slab is at or near the null point.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings:

FIG. 3 is a graphical representation of an exemplary application of the re-inversion pulse as applied in a cardiac imaging application.

DETAILED DESCRIPTION

Figure 1:
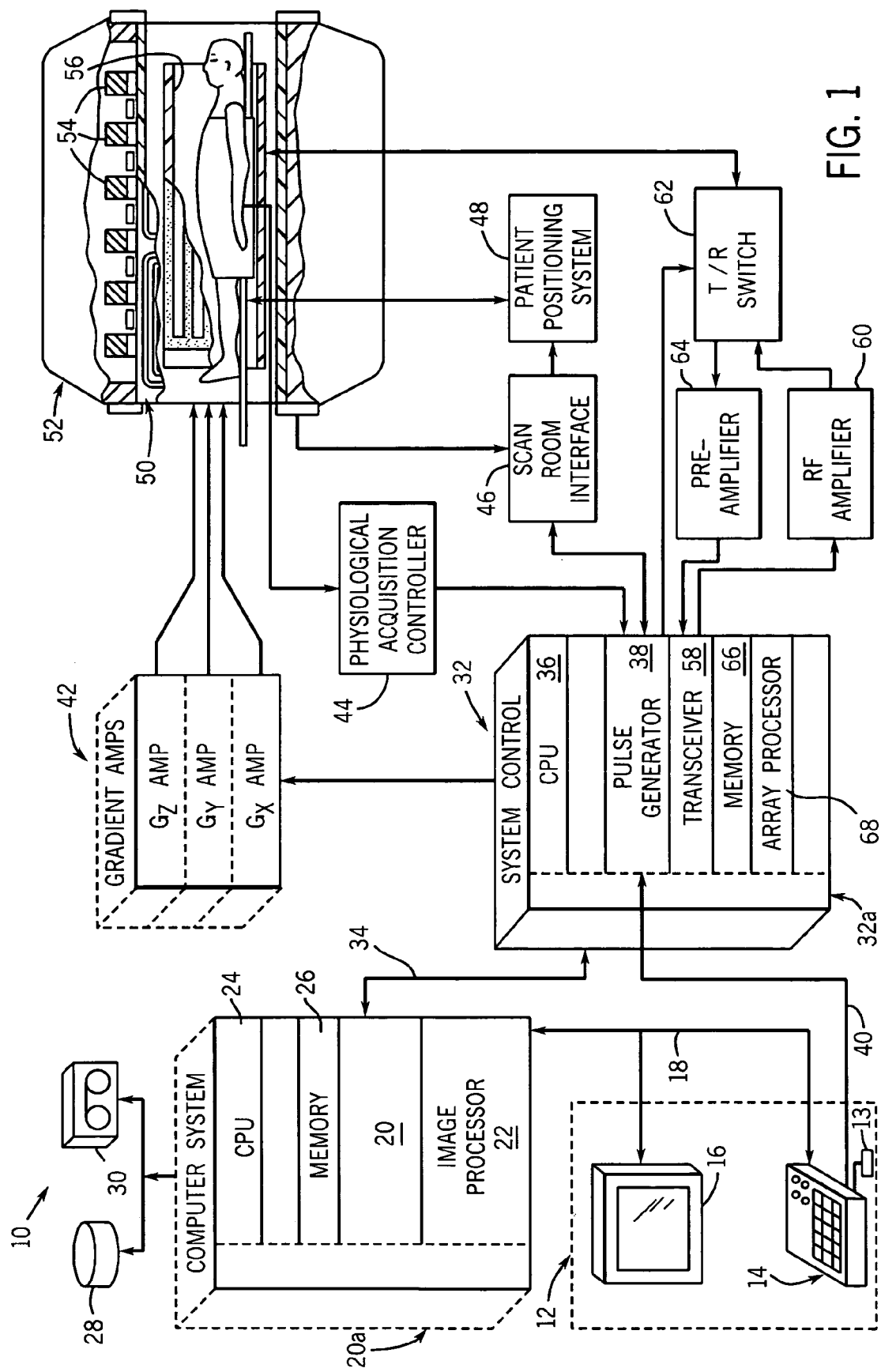
FIG. 1 is a schematic block diagram of an MR imaging system for use with the present invention.

Referring to FIG. 1, the major components of a preferred magnetic resonance imaging (MRI) system 10 incorporating the present invention are shown. The operation of the system is controlled from an operator console 12 which includes a keyboard or other input device 13, a control panel 14, and a display 16. The console 12 communicates through a link 18 with a separate computer system 20 that enables an operator to control the production and display of images on the screen 16. The computer system 20 includes a number of modules which communicate with each other through a backplane 20a.

These include an image processor module 22, a CPU module 24 and a memory module 26, known in the art as a frame buffer for storing image data arrays. The computer system 20 is linked to disk storage 28 and tape drive 30 for storage of image data and programs, and communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having $G_x$, $G_y$, and $G_z$ amplifiers. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either the transmit or receive mode.

The MR signals picked up by the RF coil 56 are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory, such as disk storage 28. In response to commands received from the operator console 12, this image data may be archived in long term storage, such as on the tape drive 30, or it may be further processed by the image processor 22 and conveyed to the operator console 12 and presented on the display 16.

The present invention includes a method and system suitable for use with the above reference MR system, and a pulse sequence applicable by the above referenced MR system, or any similar or equivalent system for obtaining MR images. The present invention includes a technique for efficient multi-slice acquisition with black blood contrast in fast spin echo imaging.

Figure 2:
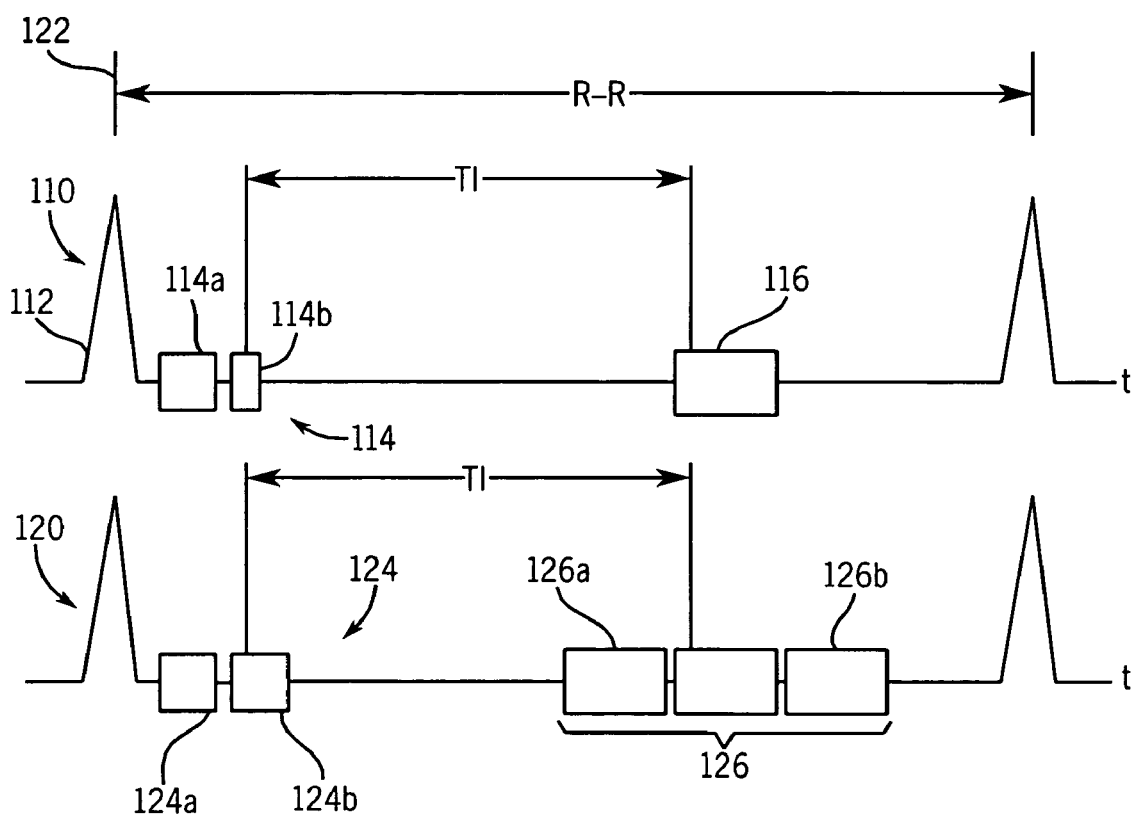
FIG. 2 is a graphical representation of a pulse sequence diagram comparing the multi-slice gated-FSE sequence with black blood contrast of the present invention to a conventional single slice sequence.

Referring to FIG. 2, a pair of ECG gated pulse sequences 10, 20 are shown on a common time axis t. Referring first to pulse sequence 10, after an ECG trigger 12 of an R-R interval, a preparation sequence 14 is applied. Preparation sequence 14 includes a non-selective inversion pulse 14a followed by a slice-selective re-inversion pulse 14b that is slice-selective only for the imaged slice. After an inversion time TI, RF excitation pulses 16 are applied to acquire data for a single spatial location.

The pulse sequence 20 of the present invention is similarly triggered by the start of an R-R interval 22 and includes a preparation sequence 24 that includes a non-selective inversion pulse 24a applicable across a slab of slices to invert spins in a longitudinal direction across the entire slab of slices having a predefined thickness. The non-selective inversion pulse 24a is immediately followed by a slice-selective re-inversion pulse 24b applicable to at least a number of the slices in the slab of slices excited by the non-selective inversion pulse 24a. In a preferred embodiment, the slice-selective inversion pulse 24b has a spatial coverage slightly greater than the non-selective inversion pulse 24a. An inversion time TI is selected such that the null point of the blood occurs in the middle of the multi-slice acquisition segment 26. In this embodiment, images for slices acquired just prior to or after the null point will have the blood in those sections partially nulled as the longitudinal magnetization will be small, but not zero.

In another embodiment, more effective suppression of the blood signal can be accomplished by modifying the flip angle of the data acquisition RF excitation pulses such that for the acquisition segment prior to the null point 26a, the excitation flip angle is set slightly less than 90°. This insures that the blood affected by this RF excitation pulse will have longitudinal magnetization below the zero line in order to have more complete blood suppression in spatially adjacent slices. Similarly, for image acquisition segments after the null point 26b, the flip angle of the RF excitation pulse is increased to slightly more than 90° in order to insure that the longitudinal magnetization of blood within the excitation slice is inverted to below the $M_z=0$ axis. This provides more complete blood suppression in adjacent slices as the blood from this slice will have the longitudinal magnetization recover through the zero axis.

It is noted that the sequence 20 can acquire data across either one R-R interval, or multiple R-R intervals, but the salient point being that data is acquired during mid-diastole. The exemplary pulse sequence 20 of FIG. 2 shows multi-slice acquisition for three slices.

Referring to FIG. 3, the three slice acquisition of FIG. 2 is shown spatially as a schematic over the heart 30 of a patient. FIG. 3 shows the slice thickness of the second re-inversion slice-selective RF pulse 24b. In this preferred embodiment, the slice thickness 32 of pulse 24b extends approximately twice the nominal slice thickness on either side of the extreme slices of the acquisition sequence 26. This width extension insures that the desired contrast is maintained by accounting for blood movement and cardiac motion between the time of the re-inversion RF pulse 24b and the data acquisition segments 26.

In order to insure that the signal from the selected regions remains unaffected by the first inversion RF pulse 24a, the slice thickness of the re-inversion pulse 24b is selected according to:

$$\text{slice thickness} = (Z_1 - Z_n) + 4 \ast \text{opslthick} \quad \text{(Eqn. 1)}$$

where $Z_1$ and $Z_n$, represents spatial locations of first and last slices selected for imaging, and opslthick represents a desired imaging slice thickness. It is preferred that the center of the second, slice-selective re-inversion slice is centered about the mid-point between $Z_1$ and $Z_n$. It is noted that the inversion time TI is selected such that the null point occurs in the middle of the multi-slice acquisition segment.

Accordingly, the present invention includes a method of multi-slice fast spin echo image acquisition with black blood contrast that includes a non-selective inversion pulse and a re-inversion pulse that is slice selective over a region encompassing a plurality of slice selections. The method includes timing execution of a series of RF excitation pulses with fast spin echo readout such that signal from black blood is near a null point to acquire data for each spatial slice.

Preferably, the plurality of slice selections include all slice selections in a slab to be imaged and the images can be acquired over more than a single breath-hold. The re-inversion pulse is preferably applied over a region having all slice selections and data are acquired for all slice selections using a single inversion pulse. In one embodiment, the method includes modifying a flip angle of the RF excitation pulses executed before and after an occurrence of the null point of the blood to insure more consistent blood suppression.

The present invention also includes a computer program for multi-slice coverage in a single acquisition with black blood $T_2$- weighted image contrast. The computer program has a set of instructions that when executed by a computer, cause the computer to generate and cause application of a non-selective inversion RF pulse to a slab of slices, each having a predefined thickness. The computer program also causes the computer to generate and cause application of a slice selective re-inversion RF pulse having a slice thickness greater than the predefined thickness of a single slice and apply an inversion time so that a null point of blood within the slab occurs in a middle of an acquisition. A series of RF excitation pulses is applied and MR data is acquired for each slice in the slab.

In a preferred embodiment, the slice thickness of the re-inversion pulse generated by the computer program is selected greater than the slab of slices to allow for cardiac motion between application of the slice-selective RF pulse and the acquisition of MR data. In one embodiment, the RF excitation pulses as applied by the computer program have a flip angle greater than 90° for segments after the null point and less than 90° for segments before the null point. This sequence is applicable over one or more R-R intervals and the MR data can be acquired during the preferred mid-diastole portion of the R-R interval.

The present invention also includes an MR apparatus to produce consistent contrast in FSE image acquisition. The apparatus includes an MRI system having a number of gradient coils positioned about a bore of a magnet to impress a polarizing magnetic field and an RF transceiver system and an RF modulator controlled by a pulse control module to transmit RF signals to an RF coil assembly to acquire MR images. The apparatus also includes a computer programmed to apply a pulse sequence having a non-selective inversion pulse to invert spins in a longitudinal direction across an entire slab of slices and a slice selective re-inversion pulse having an implied width at least as large as that of the non-selective inversion pulse. The pulse sequence applied by the computer also has a series of excitation pulses having fast spin echo readout spaced apart from the slice selective re-inversion pulse by an inversion time to acquire data for each slice in the slab.

In a preferred embodiment, the slice-selective re-inversion pulse of the pulse sequence applied by the computer of the MR apparatus is further defined as having a width greater than that of the non-selective inversion pulse to extend on either side of the non-selective inversion pulse, and preferably extends approximately twice the nominal slice thickness on either side of the non-selective inversion pulse. To provide more consistent contrast, the series of excitation pulses may be applied with differing flip angles.

The present invention also includes a pulse sequence for use in multi-slice MR data acquisition. The pulse sequence includes a non-selective inversion pulse applicable to a slab of slices, and a slice selective re-inversion pulse applicable to at least a number of those slices. The pulse sequence also includes a series of fast spin echo readout excitation pulses applicable to the number of slices in the slab after an inversion time.

Preferably, the aforementioned inversion time is selected so that blood in the slab is at or near the null point.

The inversion time of the pulse sequence is selected to allow signal from blood in a mid-point of the number of slices to approach a null point. It is noted that the number of slices that the slice-selective re-inversion pulse spans can include all the slices in the slab of slices, fewer slices than those in the slab of slices but more than one, or more slices, or a wider spatial section than that of the slab of slices. The series of fast spin echo readout excitation pulses can have varying flip angles, such as a flip angle of less than 90° for those pulses occurring before the mid-point in the series, a flip angle of 90° for those near the mid-point of the series, and a flip angle greater than 90° for those occurring after the mid-point to provide more consistent contrast, as is desirable.

The present invention has been described in terms of the preferred embodiment, and it is recognized that equivalents, alternatives, and modifications, aside from those expressly stated, are possible and within the scope of the appending claims.

The invention claimed is:

1. A method of multi-slice image acquisition with black-blood contrast comprising:
   applying a non-selective inversion pulse;

applying a re-inversion pulse that is slice-selective over a region encompassing a plurality of slice selections;

timing execution of a series of RF excitation pulses such that signal from blood is near a null point; and acquiring data for the plurality of slice selections.

2. The method of claim 1 wherein the plurality of slice selections include all slice selections in a slab to be imaged.

3. The method of claim 1 wherein the images are acquired over more than a single breath-hold.

4. The method of claim 1 wherein the re-inversion pulse is applied over a region having all slice selections in a slab and data are acquired for all slice selections in the slab using a single re-inversion pulse.

5. The method of claim 1 further comprising creating the inversion pulse with slice thickness given by:

slice thickness=$(Z_1-Z_n)$+4*opslthick, where $Z_1$ and $Z_n$ represents spatial locations of first and last slices selected and opsithick represents a desired imaging slice thickness.

6. The method of claim 5 further comprising creating the re-inversion pulse with a center centered about a midpoint between $Z_1$ and $Z_n$.

7. The method of claim 1 wherein the timing step includes selecting an inversion time TI such that the null point of the blood occurs near a center of the multi-slice acquisition.

8. The method of claim 1 further comprising modifying a flip angle of RF excitation pulses executed before and after an occurrence of the null point of the blood to improve blood suppression.

9. The method of claim 8 further comprising modifying the flip of RE excitation pulses occurring before the null point to slightly less than 90° and those occurring after the null point to slightly more than 90°.

10. A computer program stored on a computer readable storage medium and having a set of instructions that when executed by a computer cause the computer to:

(A) generate and cause application of a non-selective inversion RF pulse to a slab of slices each having a thickness;

(B) generate and cause application of a slice-selective re-inversion RF pulse having a slice thickness greater than the thickness of a single slice;

(C) apply an inversion time;

(D) apply RE excitations; and (E) acquire MR data.

11. The computer program of claim 10 wherein the slice thickness of the re-inversion pulse is selected greater than the slab of slices to allow for cardiac motion between the application of the slice-selective re-inversion RE pulse, and the acquisition of MR data.

12. The computer program of claim 10 wherein the RE excitations have a flip angle greater than 90° for segments after a null point and less than 90° for segments before the null point.

13. The computer program of claim 10 wherein acts (A)-(E) are carried out over one or more R-R intervals.

14. The computer program of claim 10 wherein the MR data is acquired during mid-diastole of an R-R interval.

15. An MR apparatus to produce consistent contrast in image acquisition comprising:

a magnetic resonance imaging (MRI) system having a plurality of gradient coils positioned about a bore of a magnet to impress a polarizing magnetic field and an RF transceiver system and an RF switch controlled by a pulse module to transmit RF signals to an RF coil assembly to acquire MR images; and a computer programmed to apply a pulse sequence having:

a non-selective inversion pulse to invert spins in a longitudinal direction across an entire slab of slices;

a slice-selective re-inversion pulse having an implied width at least as large as that of the non-selective inversion pulse; and a series of excitation pulses spaced apart from the slice-selective re-inversion pulse by an inversion time.

16. The MR apparatus of claim 15 wherein the slice-selective re-inversion pulse of the pulse sequence is further defined as having a width greater than that of the non-selective inversion pulse to extend on either side of the non-selective inversion pulse.

17. The MR apparatus of claim 16 wherein the slice-selective re-inversion pulse extends approximately twice the nominal slice thickness on either side of the non-selective inversion pulse.

18. The MR apparatus of claim 15 wherein the inversion time of the pulse sequence is selected such that blood signal is close to a null point.

19. The MR apparatus of claim 18 wherein the series of excitation pulses have therein excitation pulses with differing flip angles.

20. The MR apparatus of claim 19 wherein excitation pulses occurring near a mid-point of the series have a flip angle near 90° and excitation pulses occurring before a mid-point have a flip angle less than 90° and excitation pulses occurring after the mid-point have a flip angle more than 90°.

* * * * *

UNITED STATES PATENT AND TRADEMARK OFFICE
CERTIFICATE OF CORRECTION

PATENT NO.        : 7,546,155 B2                                    Page 1 of 1
APPLICATION NO. : 09/682685
DATED             : June 9, 2009
INVENTOR(S)       : Foo et al.

It is certified that error appears in the above-identified patent and that said Letters Patent is hereby corrected as shown below:

Col. 7, line 19 (Claim 5), delete "selected and" and
    substitute therefore -- selected for imaging, and --;

Col. 7, line 33 (Claim 9), delete "RE" and
    substitute therefore -- RF --; and Col. 7, line 45 (Claim 10), delete "(I)) apply RE" and
    substitute therefore -- (D) apply RF --.

Col. 8, line 2 (Claim 11), delete "RE" and
    substitute therefore -- RF --; and Col. 8, line 4 (Claim 12), delete "RE" and
    substitute therefore -- RF --.

Signed and Sealed this

Twenty-eighth Day of July, 2009

JOHN DOLL
*Acting Director of the United States Patent and Trademark Office*